United States Patent [19]

Farquharson et al.

[11] Patent Number: 4,643,763

[45] Date of Patent: Feb. 17, 1987

[54] HERBICIDAL CYCLOHEXANE-1,3-DIONE DERIVATIVES

[75] Inventors: Graeme J. Farquharson, Carlton; Keith G. Watson, Blackburn North; Graham J. Bird, Ascot Vale, all of Australia

[73] Assignee: ICI Australia Limited, Victoria, Australia

[21] Appl. No.: 774,527

[22] Filed: Sep. 10, 1985

[30] Foreign Application Priority Data

Sep. 28, 1984 [AU] Australia ............... PG7377

[51] Int. Cl.⁴ .............. A01N 31/08; A01N 33/04; C07C 131/00
[52] U.S. Cl. ......................... 71/98; 71/105; 71/106; 71/107; 71/114; 71/121; 564/17; 564/51; 564/52; 564/74; 564/86; 564/88; 564/99; 564/157; 564/158; 564/165; 564/169; 564/185; 564/257; 558/230; 558/234; 558/250; 558/408; 558/409; 558/414; 558/418; 560/10; 560/20; 560/22; 560/67; 560/108; 560/23; 562/250; 568/255; 560/35; 562/440; 568/327; 560/53; 260/502.6; 560/65
[58] Field of Search ............. 564/257, 17, 51, 74, 564/86, 99, 157, 165, 185; 260/465 E, 502.6; 71/98, 105, 106, 114, 121; 558/230, 234, 250, 408, 409, 418; 560/10, 20, 22, 23, 35, 65, 67, 108, 250; 562/440

[56] References Cited

U.S. PATENT DOCUMENTS 4,440,566  4/1984  Luo ........................... 71/98

Primary Examiner—Natalie Trousof
Assistant Examiner—L. Hendriksen
Attorney, Agent, or Firm—Cushman, Darby & Cushman

[57] ABSTRACT

The invention concerns novel compounds of the formula I

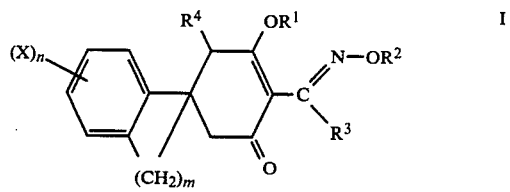

wherein:
m is an integer selected from 1 to 4;
n is zero or an integer selected from 1 to 4;
x are selected from halogen, nitro, cyano, alkyl, substituted alkyl, hydroxy, alkoxy, alkylthio, sulfamoyl, substituted sulfamoyl, amino, substituted amino, the group $-(CH_2)_pC(=A)Z$ in which p is zero or one A is oxygen or sulfur, and Z is hydrogen, hydroxy, alkoxy, alkylthio, alkyl, substituted alkyl, amino or substituted amino; the group $-NHC(=B)NR^7R^8$ in which B is oxygen or sulfur and $R^7$ and $R^8$ are hydrogen or alkyl;
$R^1$ is selected from hydrogen, acyl and an inorganic or organic cation;
$R^2$ is selected from alkyl, substituted alkyl, alkenyl, haloalkenyl, alkynyl and haloalkynyl;
$R^3$ is selected from alkyl, fluoroalkyl, alkenyl, alkynyl, and phenyl; and
$R^4$ is selected from hydrogen, halogen, alkyl, cyano and alkoxycarbonyl.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

12 Claims, No Drawings

HERBICIDAL CYCLOHEXANE-1,3-DIONE DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C R Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464 655 and its equivalents such as U.K. Pat. No. 1 461 170 and U.S. Pat. No. 3,950,420.

More recently, at the 1980 British Crop Protection Conference ("1980 British Crop Protection Conference—Weeds, Proceedings Vol 1, Research Reports", pp 39 to 46, British Crop Protection Council, (1980), a new cyclohexane-1,3-dione grass herbicide code named NP 55 (2-N-ethoxybutrimidoyl)-5-(2-ethylthiopropyl)-3-hydroxy-2-cyclohexen-1-one) was announced. This compound is disclosed in Australian Pat. No. 503 917 and its equivalents.

It is also know that spirocyclo-hexane-3,5-dione derivatives exhibit certain herbicidal properties (Chemical Abstract Vol. 85: 77859). It has now been found that a new group of benzocarbocyclic spirocyclohexane-3,5-dione derivatives exhibits particularly high herbicidal activity.

Accordingly the invention provides a compound of formula I or an isomer thereof:

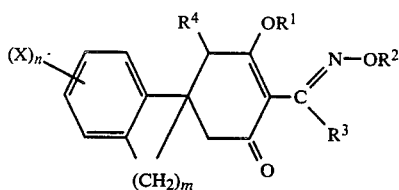

wherein:

m is an integer selected from 1 to 4;

n is zero or an integer selected from 1 to 4;

X, which may be the same or different, are independently selected from the group consisting of: halogen; nitro; cyano; $C_1$ to $C_6$ alkyl; $C_1$ to $C_6$ alkyl substituted with halogen or cyano; hydroxy; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group —$(CH_2)_pC(=A)Z$ wherein p is zero or one, A is selected from oxygen and sulfur, and Z is selected from the group consisting of hydrogen, hydroxy, $C_1$ to $C_6$alkoxy, $C_1$ to $C_6$alkylthio, amino, N-($C_1$ to $C_6$ alkyl)amino, N,N-di($C_1$ to $C_6$ alkyl)amino, N-($C_1$ to $C_6$ alkanoyl)amino, $C_1$ to $C_6$alkyl, and $C_1$ to $C_6$ haloalkyl; the group —$NR^5R^6$ wherein $R^5$ and $R^6$ are independently selected from the group consisting of hydrogen, $C_1$ to $C_6$ alkyl, $C_2$ to $C_6$ alkanoyl, $C_2$ to $C_6$ haloalkanoyl, $C_1$ to $C_6$ alkylsulfonyl, and benzoyl; the group —$NHC(=B)NR^7R^8$ wherein B is selected from oxygen and sulfur and $R^7$ and $R^8$ are independently selected from hydrogen and $C_1$ to $C_6$ alkyl; and the group —$(CH_2)_q$— which bridges two adjacent carbon atoms of the benzene ring and wherein q is an integer selected from 3 or 4;

$R^1$ is selected from the group consisting of: hydrogen; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_3$ to $C_6$ haloalkynyl; and substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, $C_1$ to $C_6$ alkyl, $C_1$ to $C_6$ haloalkyl, $C_1$ to $C_6$ alkoxy, and $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and $R^4$ is selected from the group consisting of: hydrogen; halogen; cyano; $C_1$ to $C_6$ alkyl; and ($C_1$ to $C_6$ alkoxy)carbonyl.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N+$ wherein $R^9$, $R^{10}$, $R^{11}$ and $R^{12}$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one, or in any mixture, of the four tautomeric forms shown below.

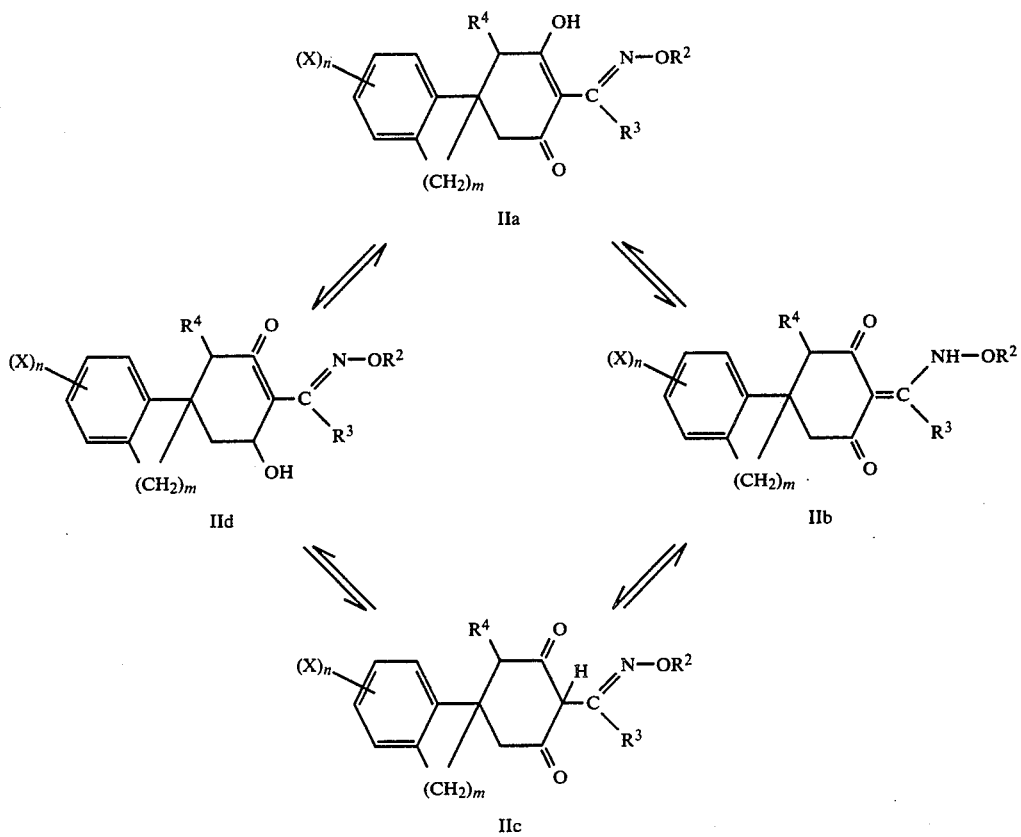

Preferred compounds of the invention include those compounds of formula I wherein:

m is an integer selected from 1, 2, and 3;

n is zero or an integer selected from 1 to 4;

X, which may be the same or different, are independently selected from the group consisting of: halogen; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group —$(CH_2)_pC(=A)Z$ wherein p is zero or one, A is oxygen or sulfur and Z is selected from the group consisting of hydroxy, $C_1$ to $C_6$ alkoxy, $C_1$ to $C_6$ alkylthio, amino, N,N-di($C_1$ to $C_6$ alkyl)amino, $C_1$ to $C_6$ alkyl; the group —$NHR^5$ wherein $R^5$ is selected from the group consisting of hydrogen, $C_2$ to $C_6$ alkanoyl, $C_2$ to $C_6$ haloalkanoyl, $C_1$ to $C_6$ alkylsulfonyl and benzoyl; and the group —$(CH_2)_q$— which bridges two adjacent carbon atoms of the benzene ring and wherein q is an integer selected from 3 or 4;

$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel, cobalt and silver, the ammonium ion and the tri- and tetra(alkyl)ammonium ions wherein alkyl is selected from $C_1$ to $C_6$ alkyl and $C_1$ to $C_6$ hydroxyalkyl;

$R^2$ is selected from the group consisting of $C_1$ to $C_6$ alkyl, $C_2$ to $C_6$ alkenyl, $C_2$ to $C_6$ alkynyl, $C_1$ to $C_6$ haloalkyl, $C_2$ to $C_6$ haloalkenyl and $C_3$ to $C_6$ haloalkynyl;

$R^3$ is selected from $C_1$ to $C_6$ alkyl;

$R^4$ is hydrogen.

More preferred compounds of the invention include those compounds of formula I wherein:

m is an integer selected from 1, 2 and 3;

n is zero or an integer selected from 1 to 4;

X, which may be the same or different, are independently selected from the group consisting of: halogen; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; $C_2$ to $C_6$ alkanoyl; $C_1$ to $C_6$ haloalkanoylamino; and the group —$(CH_2)_q$— which bridges two adjacent carbon atoms of the benzene ring and wherein q is an integer selected from 3 or 4;

$R^1$ is selected from the group consisting of hydrogen, $C_2$ to $C_6$ alkanoyl, and the alkali and alkaline earth metals;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_2$ to $C_6$ alkynyl;

$R^3$ is selected from the group consisting of $C_1$ to $C_6$ alkyl; and $R^4$ is hydrogen.

Even more preferred compounds of the invention include those compounds of formula I wherein:

m is an integer selected from 1 and 2;

n is an integer selected from 1 to 4;

X, which may be the same or different, are independently selected from the group consisting of: halogen, methyl, methoxy, methylthio, methylsulfamoyl, acetyl, propionyl, trifluoroacetylamino and the groups —(CH$_2$)$_3$— and —(CH$_2$)$_4$— which bridge two adjacent carbon atoms of the benzene ring;

R$^1$ is selected from hydrogen and the alkali metals;

R$^2$ is selected from the group consisting of C$_1$ to C$_3$ alkyl, C$_1$ to C$_3$ haloalkyl, allyl, haloallyl and propargyl;

R$^3$ is selected from C$_1$ to C$_3$ alkyl; and

R$^4$ is hydrogen.

One group of particularly preferred compounds of the invention are those compounds of formula I in which the benzene ring is substituted in the ortho and para positions (relative to the spiro junction) with methyl groups and optionally in one or both of the meta positions with another group. That is compounds of formula

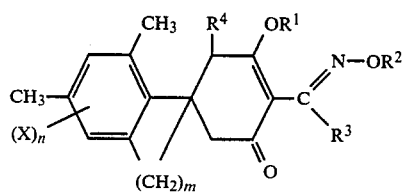

wherein:

m is an integer selected from 1 or 2;

n is zero or an integer selected from 1 and 2;

X, which may be the same or different, are independently selected from the group consisting of halogen, methyl, methylsulfamoyl, acetyl and propionyl;

R$^1$ is selected from hydrogen and the alkali metals;

R$^2$ is selected from the group consisting of C$_2$ to C$_3$ alkyl, C$_2$ to C$_3$ haloalkyl, allyl, haloallyl and propargyl;

R$^3$ is selected from C$_2$ to C$_3$ alkyl; and

R$^4$ is hydrogen.

Examples of compounds embraced by the invention include:

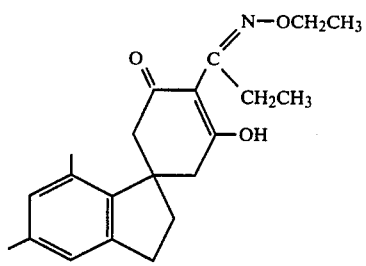

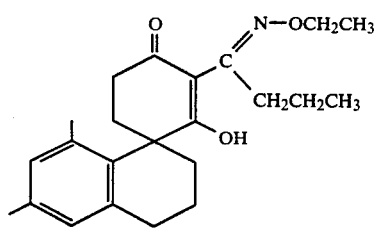

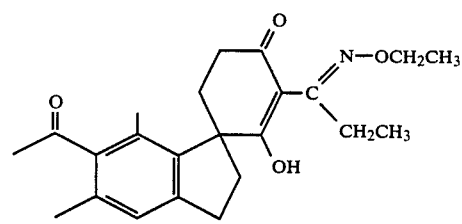

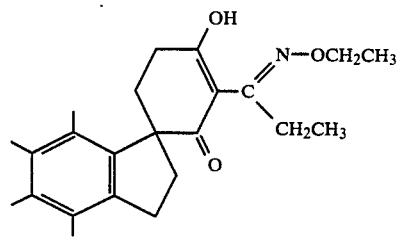

Specific examples of the compounds of the invention include those compounds detailed in Table 1 below:

TABLE 1

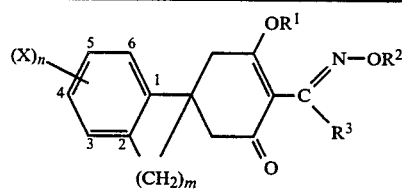

| Compound No | Xn | m | R$^1$ | R$^2$ | R$^3$ |
|---|---|---|---|---|---|
| 1 | 4,6-(CH$_3$)$_2$ | 2 | H | CH$_2$CH$_3$ | CH$_2$CH$_3$ |
| 2 | 4,6-(CH$_3$)$_2$ | 3 | H | CH$_2$CH$_3$ | CH$_2$CH$_2$CH$_3$ |
| 3 | 4,6-(CH$_3$)$_2$—5-CH$_3$CO | 2 | H | CH$_2$CH$_3$ | CH$_2$CH$_3$ |
| 4 | 3,4,5,6-(CH$_3$)$_4$ | 2 | H | CH$_2$CH$_3$ | CH$_2$CH$_3$ |
| 5 | all H | 2 | H | CH$_2$CH$_3$ | CH$_2$CH$_3$ |
| 6 | all H | 2 | H | CH$_2$CH$_3$ | CH$_2$CH$_2$CH$_3$ |
| 7 | all H | 3 | H | CH$_2$CH$_3$ | CH$_2$CH$_3$ |
| 8 | 4-CH$_3$ | 3 | H | CH$_2$CH$_3$ | CH$_2$CH$_3$ |
| 9 | 4,6-(CH$_3$)$_2$—3-CH$_3$CO | 2 | H | CH$_2$CH$_3$ | CH$_2$CH$_3$ |
| 10 | all H | 4 | H | CH$_2$CH$_3$ | CH$_2$CH$_3$ |
| 11 | 4,6-(CH$_3$)$_2$ | 1 | H | CH$_2$CH$_3$ | CH$_2$CH$_3$ |
| 12 | 4,6-(CH$_3$)$_2$ 3-(CH$_3$)$_2$NSO$_2$ | 1 | H | CH$_2$CH$_3$ | CH$_2$CH$_3$ |
| 13 | 4,6-(CH$_3$)$_2$—5-(CH$_3$)$_2$NSO$_2$ | 1 | H | CH$_2$CH$_3$ | CH$_2$CH$_3$ |
| 14 | 4,6-(CH$_3$)$_2$ 3-CH$_3$NHSO$_2$ | 1 | H | CH$_2$CH$_3$ | CH$_2$CH$_3$ |

TABLE 1-continued

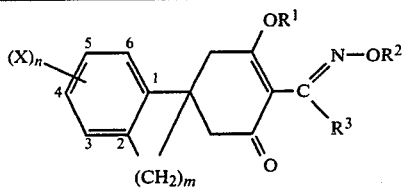

| Compound No | Xn | m | R$^1$ | R$^2$ | R$^3$ |
|---|---|---|---|---|---|
| 15 | 4,6-(CH$_3$)$_2$—5-CH$_3$NHSO$_2$ | 1 | H | CH$_2$CH$_3$ | CH$_2$CH$_3$ |
| 16 | 4,6-(CH$_3$)$_2$—3-CH$_3$CO | 1 | H | CH$_2$CH$_3$ | CH$_2$CH$_3$ |
| 17 | 4,6-(CH$_3$)$_2$—5-CH$_3$CO | 1 | H | CH$_2$CH$_3$ | CH$_2$CH$_3$ |
| 18 | 4,6-(CH$_3$)$_2$ | 1 | Na | CH$_2$CH$_3$ | CH$_2$CH$_3$ |
| 19 | 4,6-(CH$_3$)$_2$ | 1 | H | CH$_2$CH$_2$F | CH$_2$CH$_3$ |
| 20 | 4,6-(CH$_3$)$_2$ | 1 | H | CH$_2$CH=CH$_2$ | CH$_2$CH$_3$ |
| 21 | 4,6-(CH$_3$)$_2$ | 1 | H | CH$_2$C≡CH | CH$_2$CH$_3$ |
| 22 | 4,6-(CH$_3$)$_2$ | 1 | COCH$_3$ | CH$_2$CH$_3$ | CH$_2$CH$_3$ |

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a spirocyclohexane-1,3-dione of formula VI or VII. This preparation may be carried out by reacting a compound of the formula III or a compound of the formula IV with a malonic acid ester of formula V, preferably in the presence of a base, to give an intermediate of formula VI which may be isolated or hydrolysed directly to give a derivative of formula VII. Alternatively the intermediate of formula VI may be acylated without isolation as described in part B below.

Part B involves the acylation of a compound of formula VII to give a 2-acyl spirocyclohexane-1,3-dione derivative of formula XI. Alternatively Part B involves the acylation of a compound of formula VI to give a 2-acyl spirocyclohexane-1,3-dione of formula XII which may be hydrolysed directly, preferably in the presence of a base, to give a 2-acyl spirocyclohexane-1,3-dione derivative of formula XI. The acylation reaction may be carried out by reacting a spirocyclohexane-1,3-dione derivative of formula VI or VII with:

(i) an acid anhydride of formula VIII in the presence of either an alkali metal salt of the corresponding acid of formula IX or an alkoxide salt of formula X, wherein M is an alkali metal ion and R is C$_1$ to C$_6$ alkyl;

(ii) an acid anhydride of formula VIII in the presence of the corresponding acid of formula XIII, preferably in the presence of a Lewis acid or strong proton acid catalyst;

(iii) with an alkali or alkaline earth metal hydride followed by reaction with an acid anhydride of formula VIII or an acid halide of formula XIV;

(iv) an acid anhydride of formula VIII in the presence of a strong organic base such as 4-dimethylaminopyridine or imidazole.

Alternatively, this acylation reaction may be carried out by:

(v) reacting a spirocyclohexane-1,3-dione derivative of formula VI or formula VII with an acid halide of formula XIV in the presence of a base to give an intermediate O-acyl derivative of formula XV; and (vi) reacting the intermediate of formula XV with a Lewis acid or strong proton acid catalyst;

(vii) reacting the intermediate of formula XV with a suitable strong organic base such as 4-dimethylaminopyridine or imidazole.

Part C involves the formation of a compound of the invention of formula I wherein R$^1$ is hydrogen, that is a compound of formula II. This reaction may be carried out either by reacting a 2-acyl spirocyclohexane-1,3-dione of formula XI with:

(viii) an alkoxyamine derivative of formula XVI, or (ix) hydroxylamine to give an intermediate oxime derivative of formula XVII and reacting that intermediate oxime derivative of formula XVII with an alkylating agent of formula XVIII, wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part D involves the formation of a compound of the invention of formula I wherein R$^1$ is a substituent other than hydrogen.

Compounds of the invention of formula I, wherein R$^1$ forms an acyl derivative of a compound of formula II, may be prepared from the corresponding compounds of the invention of formula II by reacting with an acylation reagent of formula XIX.

Compounds of the invention of formula I wherein R$^1$ is an inorganic or organic cation may be prepared from the compounds of the invention of formula I wherein R$^1$ is hydrogen, that is, compounds of formula II, by reacting said compounds of formula II with an inorganic or organic salt. For example, the compounds of formula I wherein R$^1$ is an alkali metal ion may be prepared by reacting the appropriate compound of formula II with the appropriate alkali metal hydroxide or alkoxylate. The compounds of formula I wherein R$^1$ is a transition metal ion or an organic cation may similarly be prepared by reacting the appropriate compound of formula II with an appropriate transition metal salt or organic base. Alternatively, the compounds of formula I wherein R$^1$ is a transition metal ion or an organic cation may be prepared by reacting the appropriate compound of formula I wherein R$^1$ is an alkali metal ion with an appropriate transition metal salt or organic salt.

Accordingly, in a further aspect the invention provides a process for the preparation of a compound of formula I, as hereinbefore defined, which process comprises:

reacting a 2-acyl spirocyclohexane-1,3-dione derivative of formula XI with an alkoxyamine derivative of formula XVI to give a compound of the invention of formula II or reacting the 2-acyl spirocyclohexane-1,3-dione derivative of formula XI with hydroxylamine and alkylating the oxime intermediate of formula XVII with an alkylating agent of formula XVIII, wherein L is a leaving group, to give a compound of the invention of formula II; and optionally reacting the compound of the invention of formula II with a compound of formula XIX wherein L is a leaving group, to give a compound of the invention of formula I.

Certain of the intermediate compounds of formulae III, IV, VI, VII, XI, XII, XV and XVII are novel compounds and therefore in further embodiments the invention provides novel compounds of formula III, IV, VI, VII, XI, XII, XV and XVII and processes for the preparation thereof.

The structures of the compounds described above are detailed on the following pages.

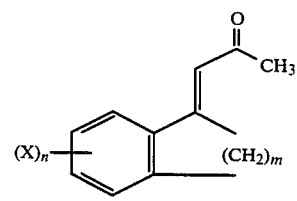  III

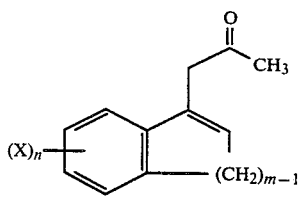  IV $R^4CH(CO_2R)_2$  V

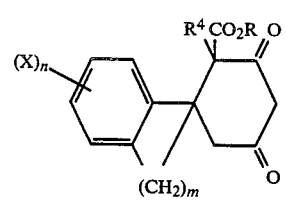  VI

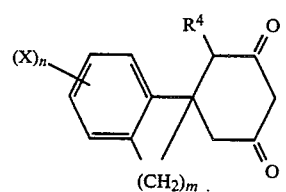  VII $(R^3CO)_2O$  VIII
$R^3CO_2M$  IX
ROM  X

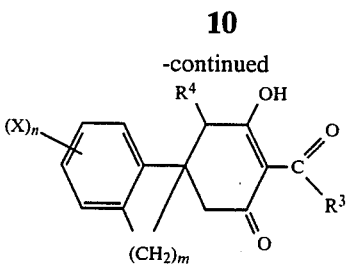  XI

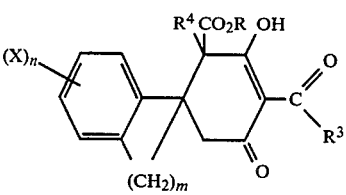  XII $R^3CO_2H$  XIII
$R^3COhal$  XIV

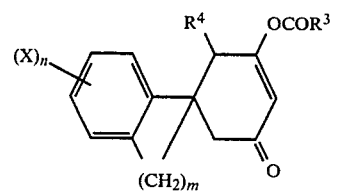  XV $H_2NOR^2$  XVI
$R^2L$  XVIII
$R^1L$  XIX

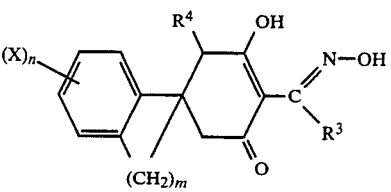  XVII

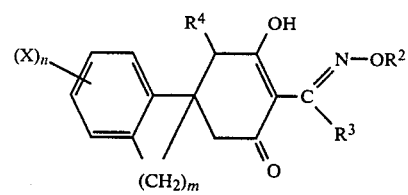  II

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyledonous weeds in cultivated crops, especially wild grasses in vegetable and cereal crops, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth, stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% to weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and triisopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 10 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivaties; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:
A. benzo-2,1,3,-thiadiazin-4-one-2,2-dioxides such as 3-isopropylbenzo-2,1,3-thiadiazin-4-one-2,2-dioxide (common name bentazon);
B. hormone herbicides and in particular the phenoxyalkanoic acids such as 4-chloro-2-methylphenoxy acetic acid (common name MCPA), 2-(Lb 2,4-dichlorophenoxy)propionic acid (common name dichlorprop), 2,4-dichlorophenoxy acetic acid (common name 2,4,-D), 2,4,5-trichlorophenoxyacetic acid (common name 2,4,5-T), 4-(4-chloro-2-methylphenoxy)butyric acid (common name MCPB), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dintrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)carbamate (common name phenmedipham) and 3-[(ethoxycarbonylamino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine). 2-chloro-4,6-di(ethylamino)-1,3,5-triazine (common name simazine) and 2-azido-4-(isopropylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. Pyridine herbicides such as 3,6-dichloropicolinic acid (common name clopyralid) and 4-amino-3,5,6-trichloropicolinic acid (common name picloram);

M. 1,2,4-triazin-5-one herbicides such as 4-amino-4,5-dihydro-3-methyl-6-phenyl-1,2,4-triazin-5-one (common name metamitron) and 4-amino-6-tert-butyl4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-isopropyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189);

T. Aryloxyphenoxypropionate herbicides such as butyl 2-[4-(5-trifluoromethyl-2-pyridyloxy)-phenoxy]propionate (common name fluazifop) and methyl 2-[4-(2,4-dichlorophenoxy)phenoxy]propionate (common name diclofop); and U. miscellaneous herbicides including N,N-dimethyl-diphenylacetamide (common name diphenamid), N-(1-naphthyl)phthalamic acid (common name naptalam) and 3-amino-1,2,4-triazole.

Examples of useful contact herbicides include:

V. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

W. organoarsenical herbicides such as monosodium methanearsonate (common name MSMA); and X. amino acid herbicides such as N-(phosphonomethyl)glycine (common name glyphosate) and its salts and esters.

The invention is now illustrated by, but in no way limited to, the following Examples.

EXAMPLE 1

4-[1-(Ethoxyimino)propyl]spiro[cyclohexane-1,1'-indan]-3,5-dione (5) and
4-[1-(ethoxyimino)butyl]spiro[cyclohexane-1,1'-indan]-3,5-dione (6)

(a) and (b)

(i) n-BuLi (32.3 ml; 1.55M in hexane) was added dropwise to a cooled (0° C.) solution of indene (5.81 gm) in anhydrous tetrahydrofuran (30 ml) under a nitrogen atmosphere. The mixture was stirred at 0° C. for 0.5 hr and at room temperature for 5 hr. A solution of propargyl bromide (5.6 ml; 80% in toluene) in anhydrous tetrahydrofuran (25 ml) was added to the cooled (0° C.) mixture which was then stirred at room temperature for 12 hr. The mixture was poured onto ice-dilute aqueous hydrochloric acid which was then extracted with diethyl ether. The dried (MgSO4) organic fraction was evaporated and the residue was heated under reflux with a mixture of ethanol (150 ml), water (50 ml), sulfuric acid (5 ml) and mercuric sulfate (1 gm) for 2 hr. The cooled mixture was filtered and the filtrate was diluted with water (200 ml). The mixture was extracted with diethyl ether. The dried (MgSO4) organic fraction was evaporated and the residue was purified by column chromatography over silica with dichloromethane elution to give, firstly, 1-acetonylindene as a brown oil, Pmr spectrum (CDCl3; δ in ppm): 2.18 (3H, s); 3.39 (2H, s); 3.64 (2H, s); 6.40 (1H, s); 7.20–7.32 (4H, m);

and secondly, 1-acetonylideneindane as a white solid, mp 54° C., Pmr spectrum (CDCl3; δ in ppm): 2.30 (3H, s); 3.03–3.30 (4H, m); 6.73 (1H, m); 7.24–7.66 (4H, m).

(ii) 1-Acetonylindene (2.4 g) was added to a solution of sodium dimethylmalonate (5.3 equiv) in anhydrous methanol (80 ml) and the mixture was stirred and heated at reflux for 12 hr. The solvent was evaporated and the residue was azeotroped with toluene. The dry residue was dissolved in anhydrous dimethylformamide (80 ml)

at 60° C. Propionic anhydride (5.3 equiv) was added and the mixture was stirred and heated at reflux for 0.5 hr. The cooled mixture was poured into a dilute aqueous hydrochloric acid solution which was then extracted with diethyl ether. The organic fraction was evaporated and the residue was heated at reflux with potassium hydroxide (5 g) in water (80 ml) for 4 hr. The cooled mixture was extracted with diethyl ether. The aqueous fraction was heated to 60° C. and was acidified by dropwise addition of a dilute aqueous hydrochloric acid solution. The cooled mixture was extracted with diethyl ether. The dried ($MgSO_4$) organic fraction was evaporated and the residue was purified by column chromatography over silica with dichloromethane elution to give 4-propionylspiro[cyclohexane-1,1'-indan]-3,5-dione as a pale yellow oil. Pmr spectrum ($CDCl_3$; δ in ppm): 1.17 (3H, t); 2.03 (2H, t); 2.64-3.24 (8H, m); 7.21-7.25 (4H, m); 18.27 (1H, s). 4-Butyrylspiro[cyclohexane-1,1'-indan]-3,5-dione was similarly prepared from 1-acetonylideneindane, sodium dimethyl malonate and n-butyric anhydride and was obtained as a pale yellow oil. Pmr spectrum ($CDCl_3$; δ in ppm): 1.00 (3H, t); 1.70 (2H, m); 2.02 (2H, t); 2.62-3.14 (8H, m); 7.20-7.25 (4H, m); 18.33 (1H, s).

(c) 4-Propionylspiro[cyclohexane-1,1'-indan]-3,5-dione (0.54 g), ethoxyamine hydrochloride (1.3 equiv), anhydrous sodium acetate (1.3 equiv) and absolute ethanol (20 ml) were stirred at room temperature for 3 hr. The mixture was poured into a very dilute aqueous hydrochloric acid solution which was then immediately extracted with diethyl ether. The dried ($MgSO_4$) organic fraction was evaporated to give 4-[1-(ethoxyimino)propyl]spiro[cyclohexane-1,1'indan]-3,5-dione (5) as a pale yellow oil. Pmr spectrum ($CDCl_3$; δ in ppm): 1.09-1.41 (6H, 2×t); 2.06 (2H, t); 2.6-3.1 (8H, m); 4.12 (2H, q); 7.2 (4H, m); 14.93 (1H, brs).

4-[1-(Ethoxyimino)butyl]spiro[cyclohexane-1,1'-indan]-3,5-dione (6) was similarly prepared from 4-butyrylspiro[cyclohexane-1,1'-indan]-3,5-dione and was obtained as a pale yellow oil. Pmr spectrum ($CDCl_3$; δ in ppm): 0.99 (3H, t); 1.32 (3H, t); 1.63 (2H, m); 2.05 (2H, t); 2.6-3.1 (8H, m); 4.12 (2H, q); 7.2 (4H, m); 15.1 (1H, brs).

EXAMPLE 2

5',7'-Dimethyl-4-[1-(ethoxyimino)propyl]spiro[cyclohexane-1,1'-indan-]-3,5-dione (1)

(i) Propargyl bromide (8.5 ml of an 80% solution in toluene) was added dropwise with stirring to an ice cold suspension of aluminium powder (2.04 g) and mercuric chloride (0.02 g) in tetrahydrofuran (50 ml). The mixture was stirred at 20° for one hour and then a solution of 5,7-dimethylindan-1-one (9.3 g) in tetrahydrofuran (20 ml) was added dropwise with stirring. After 12 hours at 20° the mixture was quenched with a saturated aqueous solution of ammonium chloride (20 ml) and then the whole reaction mixture was poured into water and extracted with diethyl ether. The organic layer was separated, dried over magnesium sulfate and concentrated to the crude product which was purified by chromatography over silica gel using carbon tetrachloride as eluent. The crude 5,7-dimethyl-1-propargylindene was dissolved in ethanol (50 ml) and together with sulfuric acid (2.5 ml), mercuric sulfate (0.50 g) and water (20 ml) was heated and stirred at 80° C. for two hours. The cooled mixture was filtered and the filtrate was diluted with water (150 ml) and then extracted with diethyl ether. The dried ($MgSO_4$) organic layer was evaporated to give a mixture of 5,7-dimethyl-1-acetonylindene and 5,7-dimethyl-1-acetonylideneindan (2.4 g).

(ii) The above mixture of ketones was reacted with sodium dimethylmalonate following the procedure given in Example 1 part (ii). Thus was obtained 5',7'-dimethyl-4-propionylspiro[cyclohexane-1,1'-indan]-3,5-dione as a pale yellow oil which was characterized by its proton magnetic resonance spectrum ($CDCl_3$; δ in ppm): 1.16 (3H, 5); 2.02 (2H, t); 2.29 (3H, s); 2.39 (3H, s); 2.3-3.5 (8H, m); 6.80 (1H, s); 6.90 (1H, s); 18.27 (1H, s).

(iii) Reaction of 5',7'-dimethyl-4-propionylspiro[cyclohexane-1,1'-indan]-3,5-dione with ethoxyamine according to the procedure described in Example 1 part (c) gave 5',7'-dimethyl-4-[1-(ethoxyimino)propyl]spiro[cyclohexane-1,1'indan]-3,5-dione (1) as a pale yellow oil which was characterized by its proton magnetic resonance spectrum and the spectroscopic data is recorded in Table 2, Example 12.

EXAMPLE 3

Compounds No. 7, 8 and 10 were prepared from the appropriate tetralone or benzosuberone following essentially the same procedure as that described in Example 2 parts (i)-(iii). The compounds were obtained as oils and were characterized by and can be identified by their proton magnetic resonance spectra. The spectroscopic data is recorded in Table 2, Example 12.

EXAMPLE 4

4',6'-Dimethyl-4-[1-(ethoxyimino)propyl]spiro[cyclohexane-1,1'-benzocyclobutene]-3,5-dione (11)

(i) 4,6-Dimethylbenzocyclobut-en-1-one (5.5 g, 38 mmol) and triphenylphosphoranylidene-2-propanone (15.0 g, 47 mmol) were heated together with stirring at 180° C. for 0.5 hours. After cooling the mixture was triturated with ether, filtered and the filtrate evaporated to give 1-acetonylidene-4,6-dimethylbenzocyclobutene as a pale brown solid (5.7 g, 81%). Pmr spectrum ($CDCl_3$, δ in ppm): 2.30 (6H, s); 2.35 (3H,s); 3.94 (2H, s); 6.25 (1H, s); 6.86 (2H, s).

(ii) 1-Acetonylidene-4,6-dimethylbenzocyclobutene was converted through to 4',6'-dimethyl-4-[1-(ethoxyimino)propyl]spiro[cyclohexane-1,1'-benzocyclobutene]-3,5-dione (11) following essentially the same procedure was described in Example 1 parts (ii) and (c). The compound was isolated as an oil and was characterized by its recorded in Table 2 Example 12.

EXAMPLE 5

4',6'-Dimethyl-3'-dimethylsulfamoyl-4-[1-(ethoxyimino)propyl]spiro[cyclohexane-1,1'-benzocyclobutene]-3,5-dione (12) and
4',6'-dimethyl-5'-dimethylsulfamoyl-4-[1-(ethoxyimino)propyl]spiro[cyclohexane-1,1'-benzocyclobutene]-3,5-dione (13)

(i) To an ice-cooled stirred solution of 4',6'-dimethyl-4-propionylspiro[cyclohexane-1,1'-benzocyclobutene]-3,5-dione (0.8 g, 2.8 mmol) in methylene chloride (10 ml) was added chlorosulfonic acid (3 ml) over a period of 0.5 hours. The mixture was stirred at 5° C. for 1 hour and then poured into ice. The organic layer was separated, washed with water then dried ($Na_2SO_4$) and evaporated to a brown oil (1.0 g). The crude chlorosulfonyl compound was dissolved in ethanol (20 ml) and treated at room temperature with ethanolic dimethylamine (0.62 ml of 40% solution, 4.8 mmol). After 4 hours the solution was diluted with water and extracted with methylene chloride. The organic layer was separated, dried (Na$_2$SO$_4$) and concentrated to give a mixture of 4',6'-dimethyl-3'-dimethylsulfamoyl-4-propionylspiro[cyclohexane-1,1'-benzocyclobutene]-3,5-dione and 4',6'-dimethyl-5'-dimethylsulfamoyl-4-propionylspiro[cyclohexane-1,1'-benzocyclobutene]-3,5-dione as a pale brown oil. Pmr spectrum (CDCl$_3$, δ in ppm): 1.16 (3H, t); 2.21 (3H, s); 2.52 (3H, s); 2.4–3.2 (4H, m); 2.78 (6H, s); 3.19 (2H, q); 3.22 (2H, s); 6.91 (1H, s); 18.05 (1H, s).

(ii) Treatment of the mixture of triones described in part (i) above with ethoxyamine according to the procedure given in Example 1 part (c) gave a mixture of the title compounds (12) and (13) in approximately equal proportions. The mixture was isolated as an oil and was characterized by its proton nuclear magnetic resonance spectrum which is recorded in Table 2, Example 12.

EXAMPLE 6

Compounds No. 14 and 15 were prepared as a mixture following a similar procedure to that given in Example 5 part (i) and (ii). The mixture was characterized by its proton magnetic resonance spectrum which is recorded in Table 2, Example 12.

EXAMPLE 7

4'-Acetyl-5',7'-dimethyl-4-[1-(ethoxyimino)propyl]-spiro[cyclohexane-1,1'-indan]-3,5-dione (9) and
6'-acetyl-5',7'-dimethyl-4-[1-(ethoxyimino)propyl]-spiro[cyclohexane-1,1'-indan]-3,5-dione (3)

(i) To a stirred suspension of aluminium trichloride (4.8 g, 33 mmol) in 1,2-dichloroethane (80 ml) at 20° C. was added a solution of 5', 7'-dimethyl-4-propionylspiro[cyclohexane-1,1'-indan]-3,5-dione (3.2 g, 11 mmol) in dichloroethane (10 ml). A solution of acetyl chloride (1.0 g, 13 mmol) in dichloroethane (10 ml) was added and the mixture was stirred at 20° C. for 12 hours. The solution was poured onto cold dilute hydrochloric acid and then extracted with diethyl ether. The ether layer was separated, dried (MgSO$_4$) and evaporated and the crude product was purified by passage through silica gel eluting with methylene chloride. A mixture of 4'-acetyl-5',7'-dimethyl-4-propionylspiro[cyclohexane-1,1'-indan]-3,5-dione and 6'-acetyl-5',7'-dimethyl-4-propionylspiro[cyclohexane-1,1'-indan]-3,5-dione was obtained as a colourless oil (1.0 g, 29%). Pmr spectrum (CDCl$_3$, δ in ppm): 1.16 (3H, t); 1.9–3.3 (17H, complex m); 3.09 (2H, q); 6.84 (0.6H, s); 6.93 (0.4H, s); 18.26 (1H, s).

(ii) The mixture of two isomeric triones from part (i) above was treated directly with ethoxyamine following the procedure given in Example 1 part (c). The product was a mixture of 4'-acetyl-5'7'-dimethyl-4-[1-(ethoxyimino)propyl]spiro[cyclohexane-1,1'-indan]-3,5-dione (3) and 6'-acetyl-5',7'-dimethyl-4-[1-(ethoxyimino)-propyl]spiro[cyclohexane-1,1'-indan]-3,5-dione (3) was isolated as an oil and characterized by its proton magnetic resonance spectrum which is recorded in Table 2, Example 12.

EXAMPLE 8

Sodium salt of 4',6'-dimethyl-4-[1-(ethoxyimino)propyl]spiro[cyclohexane-1,1'-benzocyclobutene]-3,5-dione (18)

A solution of sodium hydroxide (20 mg, 0.5 mmol) in water (1 ml) was added to 4',6'-dimethyl-4-[1-(ethoxyimino)propyl]spiro[cyclohexane-1,1'-benzocyclobutene]-3,5-dione (11) (160 mg, 0.5 mmol). The mixture was stirred until homogeneous and then the water was removed under reduced pressure by azeotropic distillation using toluene. The sodium salt (18) was obtained as a brown non-crystalline solid after removal of all the water.

EXAMPLE 9

Compounds Nos. 19, 20 and 21 were obtained by treating 4',6'-dimethyl-4-propionylspiro[cyclohexane-1,1'-benzocyclobutene]-3,5-dione (Example 4, part (ii)) with the appropriate alkoxyamine following exactly the same procedure as described in Example 1 part (c). The compounds were each isolated as an oil and were characterized chiefly by their proton magnetic resonance spectra which are recorded in Table 2, Example 12.

EXAMPLE 10

3'-Acetyl-4',6'-dimethyl-4-[1-(ethoxyimino)propyl]-spiro[cyclohexane-1,1'-benzocyclobutene]-3,5-dione (16) and
5'-acetyl-4',6'-dimethyl-4-[1-(ethoxyimino)propyl]-spiro[cyclohexane-1,1'-benzocyclobutene]-3,5-dione (17)

(i) Treatment of 4',6'-dimethyl-4-propionylspiro[cyclohexane-1,1'-benzocyclobutene]-3,5-dione (see Example 4) with acetylchloride in the presence of aluminium chloride following essentially the same procedure as described in Example 7 part (i) gave a mixture of the 3'- and 5'-acetyl-4',6'-dimethyl-4-propionylspiro[cyclohexane-1,1'-benzocyclobutene]-3,5-diones. Proton magnetic resonance spectrum (CDCl$_3$, δ in ppm): 1.15 (3H, t); 2.18 (3H, s); 2.35 (3H, s); 2.48 (3H, s); 2.4–3.3 (6H, m); 3.20 (2H, s); 6.88 (1H, s); 18.05 (1H, bs).

(ii) Treatment of the above mixture of triones with ethoxyamine following essentially the same procedure as described in Example 1 part (c) gave a mixture of two title compounds (16) and (17) as a brown oil which was characterized from its behaviour on thin-layer chromatography.

EXAMPLE 11

5',7'-Dimethyl-3-acetoxy-4[1-(ethoxyimino)propyl]-spiro[cyclohex-3-ene-1,1'-benzocyclobutene]-5-one (22)

A mixture of 5',7'-dimethyl-4-[1-(ethoxyimino)-propyl]spiro[cyclohexane-1,1'-benzocyclobutene]-3,5-dione (11) (130 mg), anhydrous potassium carbonate (80 mg), acetyl chloride (0.05 ml) and ethylmethyl ketone (2 ml) was warmed and stirred until thin-layer chromatography (silica/CH$_2$Cl$_2$) showed no remaining starting material. The mixture was then poured into water (20 ml) and extracted with methylene chloride. The organic layer was separated, dried (MgSO$_4$) and evaporated to give the title compound (22) as an oil which was characterized by its proton magnetic resonance spectrum which is recorded in Table 2, Example 12.

EXAMPLE 12

The majority of the compounds of the invention were obtained as oils and were characterized by and can be identified by their nuclear magnetic resonance spectra. For convenience proton magnetic resonance spectroscopic data is recorded in Table 2 below.

TABLE 2

| Compound No | Proton Magnetic Resonance Spectrum (CDCl$_3$, δ in ppm) |
| --- | --- |
| 1 | 1.17(3H,t); 1.33(3H,t); 2.07(2H,t; 2.29(3H,s); 2.39(3H,s); 2.4–3.2(8H,m); 4.12(2H,q); 6.80(1H,s); 6.90(1H,s); 14.7(1H,bs). |
| 3 and 9 (mixture) | 1.17(3H,t); 1.33(3H,t); 2.0–3.2(19H,complex m); 4.12(2H,q); 6.84(0.6H,s); 6.93(0.4H,s); 15.06(1H,bs). |
| 5 | 1.09–1.41(6H,2xt); 2.06(2H,t); 2.6–3.1(8H,m); 4.12(2H,q); 7.2(4H,m); 14.93(1H,bs). |
| 6 | 0.99(3H,t); 1.32(3H,t); 1.63(2H,m); 2.05(2H,t); 2.6–3.1(8H,m); 4.12(2H,q); 7.2(4H,m); 15.1(1H,bs). |
| 7 | 1.09–1.41(6H,2xt); 1.86(4H,m); 2.66(6H,m); 2.95(2H,q); 4.10(2H,q); 7.17(4H,m); 15.0(1H,bs). |
| 8 | 1.23(6H,2xt); 1.84(4H,m); 2.27(3H,s); 2.68(6H,m); 2.98(2H,q); 4.10(2H,q); 7.25(3H,m); 15.0(1H,bs). |
| 10 | 1.25(6H,m); 1.90(6H,m); 2.83(8H,m); 4.12(2H,q); 7.16(4H,m); 15.1(1H,bs). |
| 11 | 1.17(3H,t); 1.32(3H,t); 2.15(3H,s); 2.29(3H,s); 2.3–3.1(8H,complex m); 4.13(2H,q); 6.76(2H,s); 14.98(1H,bs). |
| 12 and 13 (mixture) | 1.17(3H,t); 1.34(3H,t); 2.22(3H,s); 2.53(3H,s); 2.5–3.3(6H,m); 3.24(2H,s); 4.14(2H,q); 6.95(1H,s); 15.1(1H,bs). |
| 14 and 15 (mixture) | 1.17(3H,t); 1.34(3H,t); 2.21(3H,s); 2.53(3H,s); 2.61(3H,d J 5.3 Hz); 2.4–3.3(6H,m); 3.25(2H,s); 4.14(2H,q); 4.9(1H,d) 6.94(1H,s); 15.2(1H,bs). |
| 16 and 17 (mixture) | Not recorded |
| 18 | Not recorded |
| 19 | 1.18(3H,t); 2.17(3H,s); 2.31(3H,s); 2.97(8H,m), 4.53(4H,m); 6.78(2H,m); 14.04(1H,bs). |
| 20 | 1.18(3H,t); 2.16(3H,s); 2.30(3H,s); 2.96(8H,m), 4.55(2H,d); 5.36(2H,m); 5.85(1H,m); 6.78(2H,m); 14.65(1H,bs). |
| 21 | 1.17(3H,t); 2.17(3H,s); 2.31(3H,s); 2.53(1H,t); 2.97(8H,m); 4.67(2H,d); 6.79(2H,m); 13.9(1H,bs). |
| 22 | 0.98(3H,t); 1.26(3H,t); 2.15(3H,s); 2.19(3H,s); 2.30(3H,s); 2.77(8H,m); 4.13(2H,q); 6.78(2H,m); 14.0(1H,bs). |

EXAMPLE 13

This non-limiting Example illustrates the preparation of formulations of the compounds of the invention.

(a) Emulsifiable Concentrate

Compound No 5 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.
("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 18 (5 parts by weight and "Dyapol" PT (1 part by weight) were added to an aqueous solution (94 parts by weight) of "Teric" N8 and the mixture was ball milled to produce a stable aqueous suspension which may be diluted with water to the required conclentraltion to give an aqueous suspension which may be diluted with water to the required concentration to give an aqueous suspension which may be applied by spraying. ("Dyapol" is a Trade mark and "Dyapol" PT is an anionic suspending agent; "Teric" N8 is a product of ethoxylation of nonylphenol.)

(c) Emulsifiable Concentrate

Compound No 5 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 5 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "aerosol" OT/B is a formulation of the dioctyl ester of sodium sulfosuccinic acid.)

(e) Dusting Powder

Compound No 5 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 14, 15 and 16, in the evaluation of the pre-emergence and post-emergence herbicidal activity of the compounds.

EXAMPLE 14

The pre-emergent herbicidal activity of the compounds of the invention formulated as described in Example 13 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| Wh | Wheat |
|---|---|
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 3
Pre-emergent Herbicidal Activity

| Compound No | Application Rate (kg/ha) | Wh | Ot | Rg | Jm | B | P | Ip | Ms | Sf |
|---|---|---|---|---|---|---|---|---|---|---|
| 1 | 1.0 | 2 | 4 | 5 | 5 | 3 | 0 | 0 | 0 | 0 |
| 1 | 0.25 | 0 | 2 | 3 | 5 | 0 | — | — | — | — |
| 1 | 0.0625 | 0 | 0 | 3 | 0 | 0 | — | — | — | — |
| 3 + 9 | 1.0 | 5 | 5 | 5 | 5 | 5 | 2 | 5 | 2 | 0 |
| 3 + 9 | 0.25 | 5 | 5 | 5 | 5 | 4 | — | — | — | — |
| 3 + 9 | 0.0625 | 3 | 5 | 4 | 5 | 5 | — | — | — | — |
| 5 | 1.0 | 3 | 5 | 5 | 4 | 4 | 0 | 0 | 0 | 0 |
| 5 | 0.25 | 1 | 5 | 5 | 1 | 2 | — | — | — | — |
| 5 | 0.0625 | 0 | 2 | 0 | 0 | 0 | — | — | — | — |
| 6 | 1.0 | 2 | 5 | 5 | 5 | 2 | 0 | 0 | 0 | 0 |
| 6 | 0.25 | 0 | 5 | 5 | 3 | 0 | — | — | — | — |
| 7 | 1.0 | 0 | 0 | 3 | 4 | 0 | 0 | 0 | 0 | 0 |
| 10 | 1.0 | 4 | 3 | 3 | 3 | 1 | 0 | 0 | 0 | 0 |
| 11 | 1.0 | 3 | 5 | 5 | 5 | 5 | 0 | 0 | 0 | 0 |
| 11 | 0.25 | 0 | 0 | 5 | 5 | 1 | — | — | — | — |
| 12 + 13 | 1.0 | 1 | 4 | 5 | 5 | 5 | 0 | 3 | 0 | 0 |
| 12 + 13 | 0.25 | 0 | 1 | 4 | 5 | 1 | — | — | — | — |
| 14 + 15 | 1.0 | 5 | 5 | 5 | 5 | 5 | 0 | 0 | 0 | 0 |
| 14 + 15 | 0.25 | 0 | 3 | 5 | 5 | 1 | — | — | — | — |
| 14 + 15 | 0.0625 | 0 | 0 | 5 | 5 | 0 | — | — | — | — |

The names of the test plants are as follows:

| Wh | Wheat |
|---|---|
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 4
Post-emergent Herbicidal Activity

| Compound No | Application Rate (kg/ha) | Wh | Ot | Rg | Jm | B | P | Ip | Ms | Sf |
|---|---|---|---|---|---|---|---|---|---|---|
| 1 | 1.0 | 4 | 5 | 5 | 5 | 3 | 0 | 0 | 0 | 0 |
| 1 | 0.25 | 1 | 5 | 5 | 5 | 3 | — | — | — | — |
| 1 | 0.0625 | 0 | 5 | 4 | 4 | 0 | — | — | — | — |
| 3 + 9 | 1.0 | 5 | 5 | 5 | 5 | 5 | 0 | 0 | 0 | 0 |
| 3 + 9 | 0.25 | 5 | 5 | 5 | 5 | 5 | — | — | — | — |
| 3 + 9 | 0.0625 | 5 | 5 | 5 | 5 | 5 | — | — | — | — |
| 5 | 1.0 | 4 | 5 | 5 | 5 | 5 | 0 | 0 | 0 | 0 |
| 5 | 0.25 | 3 | 5 | 5 | 5 | 5 | — | — | — | — |
| 5 | 0.0625 | 3 | 5 | 4 | 5 | 4 | — | — | — | — |
| 6 | 1.0 | 1 | 5 | 5 | 5 | 5 | 0 | 0 | 0 | 0 |
| 6 | 0.25 | 0 | 5 | 4 | 5 | 4 | — | — | — | — |
| 6 | 0.0625 | 0 | 5 | 1 | 2 | 0 | — | — | — | — |
| 7 | 1.0 | 0 | 4 | 3 | 4 | 1 | — | — | — | — |
| 7 | 0.25 | 0 | 1 | 2 | 4 | 0 | — | — | — | — |
| 8 | 1.0 | 0 | 4 | 3 | 5 | 4 | — | — | — | — |
| 8 | 0.25 | 0 | 0 | 0 | 4 | 4 | — | — | — | — |
| 11 | 1.0 | 4 | 5 | 5 | 5 | 5 | 0 | 0 | 0 | 0 |
| 11 | 0.25 | 0 | 4 | 5 | 5 | 3 | — | — | — | — |
| 11 | 0.0625 | 0 | 1 | 1 | 5 | 0 | — | — | — | — |
| 12 + 13 | 1.0 | 4 | 5 | 5 | 5 | 5 | 1 | 0 | 3 | 1 |
| 12 + 13 | 0.25 | 4 | 4 | 5 | 5 | 5 | — | — | — | — |
| 12 + 13 | 0.0625 | 3 | 4 | 5 | 5 | 4 | — | — | — | — |
| 14 + 15 | 1.0 | 4 | 5 | 5 | 5 | 5 | 0 | 0 | 2 | 0 |
| 14 + 15 | 0.25 | 3 | 5 | 5 | 5 | 5 | — | — | — | — |
| 14 + 15 | 0.0625 | 2 | 5 | 5 | 5 | 4 | — | — | — | — |

EXAMPLE 15

The post-emergent herbicidal activity of the compounds of the invention formulated as described in Example 13 was assessed by the following procedure.

The seeds of the test species werd sown in rows 2 cm deep in soil contained in seed boxes. The monocotyledonous plants and the dicotyledonous plants were down in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

EXAMPLE 16

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 5 below. Damage to test plants was assessed after 14 days on a scale of 0 to 5 wherein 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal camage was carried out after 21 days using the same scale of 0 to 5 as the post-emergence test. In both cases the degree of herbicidal damage was assessed by comparison with untreated control palnts. The results are given in Table 5 below. A dash (-) means no experiment was carried out.

The names of the test plants were as follows:

| | | |
|---|---|---|
| Mz | Maize | |
| Ww | Winter wheat | |
| Rc | Rice | |
| Br | Barley | |
| Av | *Avena fatua* | |
| Dg | *Digitaria sanguinalis* | |
| Al | *Alopecurus myosuroides* | |
| St | *Setaria viridis* | |
| Ec | *Echinochloa crus-galli* | |
| Sh | *Sorghum halepense* | |
| Ag | *Agropyron repens* | |

TABLE 5

| Compound No | APPLICATION Method Rate (kg/ha) | TEST PLANT | | | | | | | | | | |
|---|---|---|---|---|---|---|---|---|---|---|---|---|
| | | Mz | Ww | Rc | Br | Av | Dg | Al | St | Ec | Sh | Ag |
| 1 | 0.20 | 5 | 1 | 4 | 3 | 5 | 5 | 5 | 5 | 5 | 4 | 0 |
| 1 | 0.05 | 5 | 0 | 4 | 0 | 4 | 4 | 4 | 4 | 4 | 3 | 0 |
| 1 | 0.02 | — | — | — | — | 3 | 3 | 4 | 4 | 4 | 0 | 0 |
| 5 | 0.20 | 4 | 2 | 4 | 4 | 4 | 2 | 4 | 4 | 4 | 3 | 0 |
| 5 | 0.05 | 4 | 0 | 4 | 4 | 4 | 2 | 4 | 3 | 4 | 2 | 0 |
| 6 | 0.40 | 4 | 1 | 4 | 4 | 5 | 4 | 4 | 4 | 4 | 3 | 0 |
| 6 | 0.10 | 4 | 0 | 4 | 2 | 4 | 2 | 4 | 3 | 4 | 2 | 0 |
| 7 | 0.20 | 4 | 2 | 3 | 3 | 3 | 3 | 3 | 3 | 3 | 1 | 0 |
| 7 | 0.10 | 3 | 0 | 1 | 1 | 2 | 2 | 2 | 1 | 3 | 0 | 0 |
| 8 | 0.40 | 3 | 0 | 2 | 3 | 2 | 3 | 3 | 3 | 3 | 2 | 1 |
| 8 | 0.20 | 3 | 0 | 3 | 3 | 2 | 2 | 1 | 2 | 3 | 0 | 0 |
| 11 | 0.20 | 5 | 2 | 3 | 4 | 4 | 3 | 4 | 4 | 4 | 4 | 0 |
| 11 | 0.10 | 5 | 2 | 3 | 3 | 3 | 2 | 3 | 3 | 4 | 3 | 1 |
| 11 | 0.05 | 3 | 0 | 2 | 3 | 2 | 2 | 3 | 3 | 4 | 3 | 0 |

We claim:

1. A compound of formula I

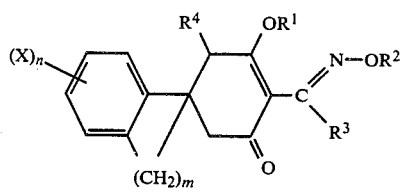

wherein:
m is an integer selected from 1 to 4;
n is zero or an integer selected from 1 to 4;
X, which may be the same or different, are independently selected from the group consisting of: halogen; nitro; cyano; $C_1$ to $C_6$ alkyl; $C_1$ to $C_6$ alkyl substituted with halogen or cyano; hydroxy; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group —$(CH_2)_pC(=A)Z$ wherein p is zero or one, A is selected from oxygen and sulfur, and Z is selected from the group consisting of hydrogen, hydroxy, $C_1$ to $C_6$ alkoxy, $C_1$ to $C_6$ alkylthio, amino, N-($C_1$ to $C_6$ alkyl)amino, N,N-di($C_1$ to $C_6$ alkyl)amino, N-($C_1$ to 6 alkanoyl)amino, $C_1$ to $C_6$ alkyl, and $C_1$ to $C_6$ haloalkyl; the group —$NR^5R^6$ wherein $R^5$ and $R^6$ are independently selected from the group consisting of hydrogen, $C_1$ to $C_6$ alkyl, $C_2$ to $C_6$ alkanoyl, $C_2$ to $C_6$ haloalkanoyl, $C_1$ to $C_6$ alkylsulfonyl, and benzoyl; the group —$NHC(=B)NR^7R^8$ wherein B is selected from oxygen and sulfur and $R^7$ and $R^8$ are independently selected from hydrogen and $C_1$ to $C_6$ alkyl; and the group —$(CH_2)_q$— which bridged two adjacent carbon atoms of the benzene ring and wherein q is an integer selected from 3 or 4;
$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy: benzenesulfonyl and substituted benzenesulfonyl wherein the benzene ring is substituted with from one to three substituents selected from the group consisting of halogen, nitro, $C_1$ to $C_6$ alkyl and $C_1$ $C_6$ alkoxy; and an inorganic or an organic cation selected from the alkali metals, the alkaline earth metals the transition metals the ammonium ion and the tri- and tetra(alkyl)ammonium ions wherein alkyl is selected from $C_1$ to $C_6$ alkyl and $C_1$ to $C_6$ hydroxyalkyl;
$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl, $C_3$ to $C_6$ haloalkynyl; and substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, $C_1$ to $C_6$ alkyl, $C_1$ to $C_6$ haloalkyl, $C_1$ to $C_6$ alkoxy, and $C_1$ to $C_6$ alkylthio;
$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and
$R_4$ is selected from the group consisting of: hydrogen; halogen; cyano; $C_1$ to $C_6$ alkyl; and ($C_1$ to $C_6$ alkoxy)carbonyl.

2. A compound according to claim 1 wherein:
m is an integer selected from 1 to 4;
n is zero or an integer selected from 1 to 4;
X, which may be the same or different, are independently selected from the group consisting of: halogen; nitro; cyano; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl; N,Ndi($C_1$ to $C_6$ alkyl)sulfamoyl; the group —$(CH_2)_pC(=A)Z$ wherein p is zero or one, A is selected from oxygen and sulfur, and Z is selected from the group consisting of hydrogen, hydroxy, $C_1$ to $C_6$ alkoxy, $C_1$ to $C_6$ alkylthio, amino, N-($C_1$ to $C_6$ alkyl)amino, N,N-di($C_1$ to $C_6$ alkyl)amino, N-($C_1$ to $C_6$ alkanoyl)amino, $C_1$ to $C_6$ alkyl, and $C_1$ to $C_6$ haloalkyl; the group —$NR^5R^6$ wherein $R^5$ and $R^6$ are independently selected from the group consisting of hydrogen, $C_1$ to $C_6$ alkyl, $C_2$ to $C_6$ alkanoyl, $C_2$ to $C_6$ haloalkanoyl, $C_1$ to $C_6$ alkylsulfonyl, and benzoyl; the group —NHC(=B)NR$^7$R$^8$ wherein B is selected from oxygen and sulfur and R$^7$ and R$^8$ are independently selected from hydrogen and C$_1$ to C$_6$ alkyl; and the group (CH$_2$)q— which bridges two adjacent carbon atoms of the benzene ring and wherein q is an integer selected from 3 or 4;

R$^1$ is selected from the group consisting of: hydrogen; C$_2$ to C$_6$ alkanoyl; benzoyl and substituted benzoyl wherein the benzene ring is substituted with from one to two substituents selected from the group consisting of halogen, nitro, C$_1$ to C$_6$ alkyl and C$_1$ to C$_6$ alkoxy; an alkali metal cation; an alkaline earth cation; a transition metal cation; the ammonium ion and the tri and tetra(alkyl)ammonium ions wherein alkyl is selected from C$_1$ to C$_6$ alkyl and C$_1$ to C$_6$ hydroxy-alkyl;

R$^2$ is selected from the group consisting of C$_1$ to C$_6$ alkyl, C$_1$ to C$_6$ haloalkyl, C$_2$ to C$_6$ alkenyl, C$_2$ to C$_6$ haloalkenyl and C$_3$ to C$_6$ alkynyl;

R$^3$ is selected from the group consisting of C$_1$ to C$_6$ alkyl;

R$_4$ is selected from the group consisting hydrogen, halogen, C$_1$ to C$_6$ alkyl; and (C$_1$ to C$_6$ alkoxy)carbonyl.

3. A compound according to claim 2 wherein:
m is an integer selected from 1 to 4;
n is zero or an integer selected from 1 to 4;
X, which may be the same or different, are independently selected from the group consisting of: halogen; nitro; C$_1$ to C$_6$ alkyl; C$_1$ to C$_6$ alkoxy; C$_1$ to C$_6$ alkylthio; sulfamoyl; N-(C$_1$ to C$_6$ alkyl)sulfamoyl; N,N-di(C$_1$ to C$_6$ alkyl)sulfamoyl; the group —(CH$_2$)p—C(=A)Z wherein p is zero or one, A is either oxygen or sulfur, and Z is selected from the group consisting of hydroxy, C$_1$ to C$_6$ alkoxy, C$_1$ to C$_6$ alkylthio, amino, N-(C$_1$ to C$_6$ alkyl)amino, N,N-di(C$_1$ to C$_6$ alkyl)amino, C$_1$ to C$_6$ alkyl and C$_1$ to C$_6$ haloalkyl; the group —NR$^5$R$^6$ wherein R$^5$ and R$^6$ are independently selected from the group consisting of hydrogen, C$_1$ to C$_6$ alkyl, C$_2$ to C$_6$ alkanoyl, C$_2$ to C$_6$ haloalkanoyl, C$_1$ to C$_6$ alkylsulfonyl; and the group —(CH$_2$)q— which bridges two adjacent carbon atoms of the benzene ring and wherein q is an integer selected from 3 or 4;

R$_1$ is selected from the group consisting of hydrogen; C$_2$ to C$_6$ alkanoyl; benzoyl and substituted benzoyl wherein the benzene ring is substituted with from one to two substituents selected from the group consisting of halogen, nitro, C$_1$ to C$_6$ alkyl and C$_1$ to C$_6$ alkoxy; an alkali metal cation; an alkaline earth cation; a transition metal cation; the ammonium ion and the tri and tetra(alkyl)ammonium ions wherein alkyl is selected from C$_1$ to C$_6$ alkyl and C$_1$ to C$_6$ hydroxy alkyl;

R$^2$ is selected from the group consisting of C$_1$ to C$_6$ alkyl, C$_1$ to C$_6$ haloalkyl, C$_2$ to C$_6$ alkenyl, C$_2$ to C$_6$ haloalkenyl and C$_3$ to C$_6$ alkynyl;

R$^3$ is selected from the group consisting of C$_1$ to C$_6$ alkyl; and

R$^4$ is hydrogen.

4. A compound according to claim 3 wherein:
m is an integer selected from 1 to 3;
n is zero or an integer selected from 1 to 4;
X, which may be the same or different, are independently selected from the group consisting of halogen; C$_1$ to C$_6$ alkyl; C$_1$ to C$_6$ alkoxy; C$_1$ to C$_6$ alkylthio; sulfamoyl; N-(C$_1$ to C$_6$ alkyl)sulfamoyl; N,N-di(C$_1$ to C$_6$ alkyl)sulfamoyl; C$_2$ to C$_6$ alkanoyl; C$_2$ to C$_6$ haloalkanoyl; and C$_2$ to C$_6$ haloalkanoylamino;

R$^1$ is selected form the group consisting of: hydrogen; C$_2$ to C$_6$ alkanoyl; benzoyl; an alkali metal cation; an alkaline earth metal cation; a transition metal cation; the ammonium ion and the tri and tetra(alkyl)ammonium ions wherein alkyl is selected from C$_1$ to C$_6$ alkyl and C$_1$ to C$_6$ hydroxyalkyl;

R$^2$ is selected from the group consisting of C$_1$ to C$_6$ alkyl, C$_1$ to C$_6$ haloalkyl, C$_2$ to C$_6$ alkenyl, C$_2$ to C$_6$ haloalkenyl and C$_3$ to C$_6$ alkynyl;

R$^3$ is selected from the group consisting of C$_1$ to C$_6$ alkyl; and

R$^4$ is hydrogen.

5. A compound according to claim 4 wherein:
m is an integer selected from 1 to 3;
n is zero or an integer selected from 1 to 4;
X, which may be the same or different, are independently selected from the group consisting of halogen; C$_1$ to C$_6$ alkyl; C$_1$ to C$_6$ alkoxy; sulfamoyl; N-(C$_1$ to C$_6$ alkyl)sulfamoyl; N,N-di(C$_1$ to C$_6$ alkyl)sulfamoyl and C$_2$ to C$_6$ alkanoyl;

R$^1$ is selected from the group consisting of hydrogen; C$_2$ to C$_6$ alkanoyl; benzoyl, the alkali metal cations; the alkaline earth metal cations and the transition metal cations;

R$^2$ is selected from the group consisting of C$_1$ to C$_6$ alkyl, C$_1$ to C$_6$ halo alkyl, C$_2$ to C$_6$ alkenyl, C$_2$ to C$_6$ haloalkenyl and C$_3$ to C$_6$ alkynyl;

R$^3$ is selected from C$_1$ to C$_6$ alkyl; and

R$^4$ is hydrogen.

6. A compound according to claim 5 wherein:
m is an integer selected from 1 to 3;
n is zero or an integer selected from 1 to 3;
X, which may be the same or different, are independently selected from the group consisting of C$_1$ to C$_6$ alkyl; N(C$_1$ to C$_6$ alkyl)sulfamoyl; N,N-di(C$_1$ to C$_6$ alkyl)sulfamoyl and C$_2$ to C$_6$ alkanoyl;

R$^1$ is selected from the group consisting of hydrogen; C$_2$ to C$_6$ alkanoyl; benzoyl; the alkali metal cations; the alkaline earth metal cations and the transition metal cations;

R$^2$ is selected from C$_1$ to C$_4$ alkyl, C$_1$ to C$_4$ haloalkyl, C$_2$ to C$_4$ alkenyl, C$_2$ to C$_4$ haloalkenyl and C$_3$ to C$_4$ alkynyl;

R$^3$ is selected from C$_1$ to C$_4$ alkyl; and

R$^4$ is hydrogen.

7. A compound according to claim 6 wherein:
m is an integer selected from 1 to 3;
n is an integer selected from 1 to 3;
X, which may be the same or different are independently selected from the group consisting of methyl, N-methylsulfamoyl, N,N-dimethyl-sulfamoyl, acetyl and propionyl;

R$^1$ is selected from the group consisting of hydrogen, C$_2$ to C$_6$ alkanoyl, and the alkali metal cations;

R$^2$ is selected from the group consisting of C$_1$ to C$_3$ alkyl, 2-haloethyl, allyl, 3-halo-allyl and propargyl;

R$^3$ is selected from C$_1$ to C$_4$ alkyl; and

R$^4$ is hydrogen.

8. A compound according to claim 7 selected from the group consisting of:
5′,7′-dimethyl-4-[1-(ethoxyimino)propyl]spiro[cyclohexane-1,1′-indan]-3,5-dione;
4′,6′-dimethyl-4-[1-(ethoxyimino)propyl]spiro[cyclohexane-1,1′-benzocyclobutene]-3,5-dione;

4',6'-dimethyl-3'(or 5')-N,N-dimethylsulfamoyl-4-[1-(ethoxyimino)propyl]spiro[cyclohexane-1,1'-benzocyclobutene]-3,5-dione;

4',6'-dimethyl-3'(or 5')-N-methylsulfamoyl-4-[1-(ethoxyimino)propyl]spiro[cyclohexane-1,1'-benzocyclobuten]-3,5-dione;

4'(or 6')-acetyl-5',7'-dimethyl-4-[1-(ethoxyimino)propyl]spiro[cyclohexane-1,1'-indan]-3,5-dione;

3'(or 5')acetyl-4',6'-dimethyl-4-[1-(ethoxyimino)propyl]spiro[cyclohexane-1,1'-benzocyclobutene]-3,5-dione.

9. A herbicidal composition comprising as active ingredient a herbicidally effective amount of a compound as defined according to claim 1 and an inert carrier therefor.

10. A process for severely damaging or killing unwanted plants which process comprises applying to said plants, or to the growth medium of said plants, an effective amount of a compound as defined according to claim 1.

11. A process for selectively controlling the growth of monocotyledonous weeds in dicotyledonous crops which process comprises applying to said crop, or to the growth medium of said crop, a compound as defined according to claim 1 in a amount sufficient to severely damage or kill said weeds but insufficient to substantially damage said crop.

12. A process according to claim 10 or claim 11 wherein the compound is applied at a rate in the range of from 0.005 to 20 kilograms per hectare.

* * * * *